United States Patent [19]

Roland et al.

[11] Patent Number: 4,916,068

[45] Date of Patent: Apr. 10, 1990

[54] BIOCONVERSION PRODUCTION OF ASCORBIC ACID WITH L-GALACTONO-1,4-OXIDASE

[75] Inventors: John F. Roland, Glenview, Ill.; Theodore Cayle, Fox Point, Wis.; Robert C. Dinwoodie, Glenview; David W. Mehnert, Lake Villa, both of Ill.

[73] Assignee: Kraft, Inc., Glenview, Ill.

[21] Appl. No.: 749,538

[22] PCT Filed: Oct. 19, 1984

[86] PCT No.: PCT/US84/01695
§ 371 Date: Jun. 18, 1985
§ 102(e) Date: Jun. 18, 1985

[87] PCT Pub. No.: WO85/01745
PCT Pub. Date: Apr. 25, 1985

Related U.S. Application Data

[63] Continuation-in-part of Ser. No. 543,975, Oct. 20, 1983, Pat. No. 4,595,659.

[30] Foreign Application Priority Data

Oct. 19, 1984 [WO] PCT Int'l Appl. .................. PCT/US84/01695

[51] Int. Cl.[4] .................. C12P 9/60; C12N 11/00; C12N 9/04; C12R 1/72
[52] U.S. Cl. .................................. 435/138; 435/174; 435/176; 435/177; 435/190; 435/921

[58] Field of Search ............... 435/135, 136, 138, 177, 435/174, 190, 137, 176, 921

[56] References Cited

U.S. PATENT DOCUMENTS 4,259,443  3/1981  Danehy ............................... 435/190
4,572,897  2/1986  Amotz et al. ...................... 435/177

OTHER PUBLICATIONS

Nishikimi, M. et al.; "Occurrence in Yeast of L-Galactonolactone Oxidase which is Similar to a Key Enzyme for Ascorbic Acid Biosynthesis in Animals, L--Glulonolactone Oxidase"; *Arch. Biochem. Biophy.* 191(2):479 (1978).

Bleeg, H. S. et al.; "Biosynthesis of Ascorbate in Yeast"; *European Journal of Biochemistry* 127:391 (1982).

*Primary Examiner*—Elizabeth C. Weimar
*Attorney, Agent, or Firm*—Fitch, Even, Tabin & Flannery

[57] ABSTRACT

Processes for the bioconversion production of L-ascorbic acid (Vitamin C), and to microorganisms (e.g., *Candida Norvegensis* MF-56, ATCC 20686 and *Candida Norvegensis* MF-78, ATCC 20732) and bioconversion media which are specifically adapted for such bioconversion.

9 Claims, 6 Drawing Sheets

BIOCONVERSION PRODUCTION OF ASCORBIC ACID WITH L-GALACTONO-1,4-OXIDASE

This is a Continuation-in-part of U.S. application Ser. No. 543,975, filed Oct. 20, 1983, now U.S. Pat. No. 4,595,659.

The present invention relates to methods for the production of L-ascorbic acid (Vitamin C) by fermentation, and to microorganisms and fermentation media which are particularly adapted for such fermentation.

BACKGROUND OF THE INVENTION

L-ascorbic acid is an essential dietary component for man, and is naturally present in citrus fruits and plants. It is conventionally synthesized by a variety of known methods such as that described in U.S. Pat. No. 2,265,121 to T. Reichstein using D-glucose as the starting material. Various other chemical and biological methods are known for synthesis and manufacture of L-ascorbic acid, such as those described in U.S. Pat. Nos. 2,702,808, 2,847,421 and 3,721,663, which are generally variations of the Reichstein process. However, as indicated, these are relatively complex processes which utilize glucose as starting material. Novel commercial-scale processes which utilize other starting materials would be desirable.

As described in British Patent No. 763,055, chemical-biological processes in which dehydrogenase (EC 1.3.2.3) present in enzyme animal or vegetable tissues is utilized to carry out terminal oxidation of the gamma lactones to provide L-ascorbic acid. A similar process is described in U.S. Pat. No. 4,259,443 in which hydrolyzed sugars of lactose and plant dehydrogenase enzyme (EC 1.3.2.3) derived from pea seedlings are utilized to produce L-ascorbic acid. The efficiency of the process was not disclosed but application at a commercial scale would appear to be restricted.

It has been recognized that bakers and/or brewers yeast contain L-galactono-lactone oxidase(s), an enzyme(s) believed to catalyze the terminal oxidation step in L-ascorbic acid biosynthesis in which the enzyme(s) catalyzes the oxidation of L-galactono-gamma lactone to produce L-ascorbic acid and hydrogen peroxide [*Enzymologia*; 31 #2 (1966), *Eur. J. Biochem.*; 127, 391 (1982) and others, M. Nishikimi, et al., *Arch. Biochem. BiPhys.*, 191, 479 (1978)]. Studies of the ability of yeasts grown in a nutrient medium containing D-glucose (10%) as the carbon energy source to produce ascorbic acid analogs of the enediol class have also been carried out [Heick, et al., *Can. J. Microbiol.*, 18, 597 (1972)]. In a similar study, Candida yeast strains have also been grown on sucrose, hexose or pentose to produce an ascorbic acid analog (D-erythroascorbic acid) [S. Murakawa, et al., *Agric. Biol. Chem.*, 40 (6), 1255 (1976), 41 (9) 1799 (1977)]. When the yeasts were grown in the added presence of L-galactono gamma lactone, L-ascorbic acid was also identified. Although D-erythroascorbic acid was formed from a variety of carbon sources, L-ascorbic acid was only formed when the L-sugar-lactone was also present in the fermentation medium.

It is also known that a vast amount of lactose is available as a byproduct from cheese manufacture, in the form of whey, whey permeate or milk permeate. Utilization of these byproducts has long been a source of concern to cheese manufacturers.

It has also long been known that lactose obtained from whey or other fluid milk derived byproducts may be hydrolyzed to provide glucose and galactose (e.g., U.S. Pat. Nos. 2,826,502, 2,826,503, 2,749,242, 2,681,058) and it is known that whey may be fermented to provide ethanol (e.g., Food Engineering, November, 1977 pp. 74–75; British Pat. No. 1,524,618). A new process for the manufacture of L-ascorbic acid which could be adapted to utilize dairy byproduct lactose would be particularly desirable.

Accordingly, a principal object of the present invention is to provide novel bioconversion processes for producing L-ascorbic acid which may be carried out on a commercial scale. Another object of the present invention is to provide processes which may be adapted to utilize a dairy byproduct lactose source, such as whey, whey permeate or milk permeate in the manufacture of L-ascorbic acid. A still further object of the present invention is to provide microorganisms which are capable of producing L-ascorbic acid by aerobic fermentation of ethanol in the presence of various D- and L-galactose derivatives such as L-galactono-gamma-lactone. A further object is provision of fermentation media which are particularly adapted for the microbiological manufacture Of L-ascorbic acid. These and other objects will become more apparent from the accompanying drawings and the following detailed description.

DESCRIPTION OF THE INVENTION

Figure 1:
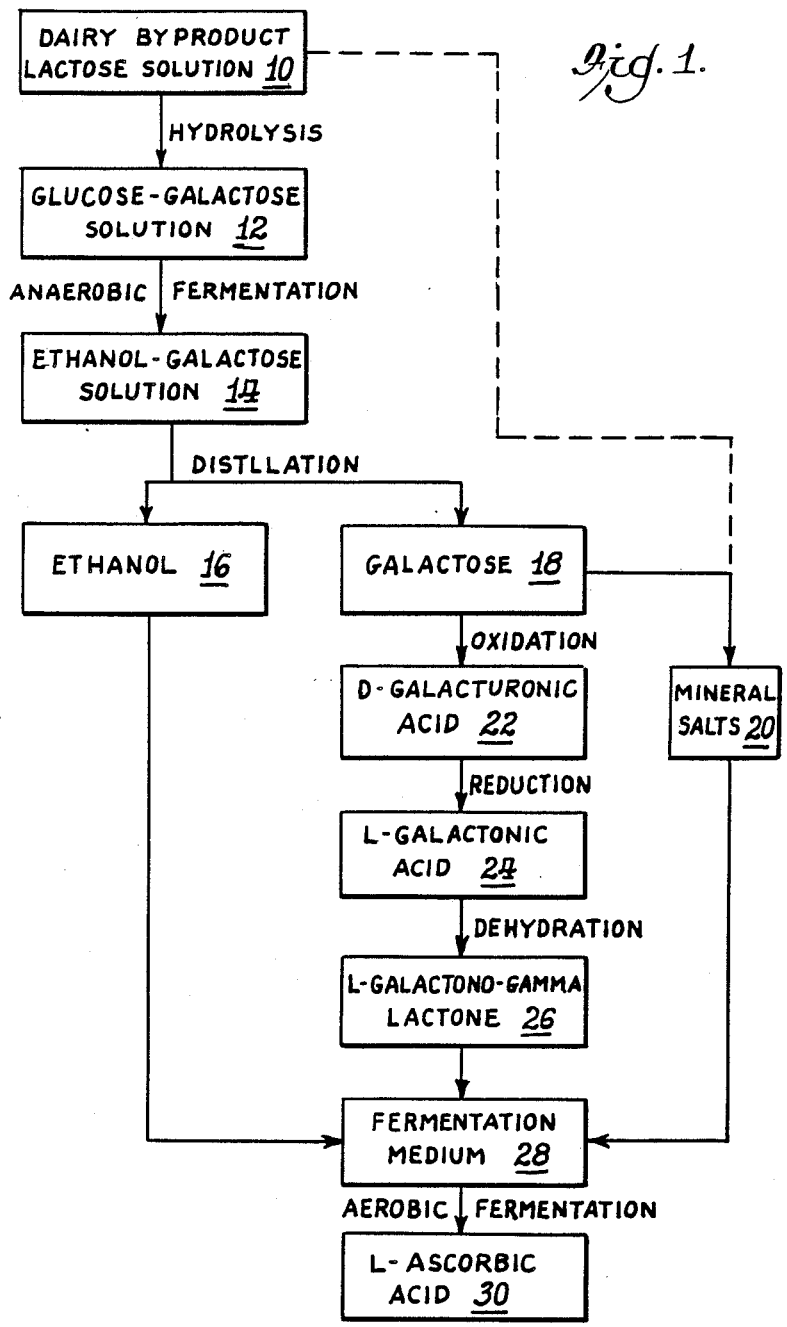
FIG. 1 is a process flow diagram of an embodiment of a method for manufacturing L-ascorbic acid from dairy byproduct lactose in accordance with the present invention.

Generally in accordance with the present invention, methods are provided for manufacture of L-ascorbic acid by the aqueous phase aerobic bioconversion of an L-galactonic substrate selected from the group consisting of L-galactono-gamma-lactone, lower alkyl esters of L-galactonic acid, L-galactonic acid, and mixtures thereof. As will be discussed in more detail hereinafter, the L-galactonic substrate may be provided in any suitable manner, such as by oxidation of D-galactose and by hydrolysis of pectinaceous materials such as citrus pectin. L-galactono-gamma-lactone is the particularly preferred L-galactonic substrate. Further in accordance with such methods, a short chain carbon fermentation energy source which may be selected from the group consisting of ethanol, glycerol and mixtures thereof is utilized in the fermentation. Ethanol is the particularly preferred carbon source.

The selection and utilization of an appropriate microorganism for the aerobic bioconversion is an important feature of the present methods. In this regard, microorganisms are desirably provided in the fermentation medium which are overproductive in L-ascorbic acid synthesis and which accumulate L-ascorbic acid from an L-galactonic substrate. By an organism which is "overproductive in L-ascorbic acid bio-synthesis" is meant an organism which either through natural mutation or genetic manipulation is capable of enhanced production of L-ascorbic acid as a metabolite at levels of at least about 0.3 grams per liter of fermentation medium based on the total volume of fermentation broth.

The production of L-ascorbic acid may be carried out by fermenting ethanol in the presence of L-galactonic substrate by particular microorganisms. Yeasts, and particularly selected yeasts of the genus Candida which are over productive in L-ascorbic acid formation from a L-galactonic substrate and which can utilize short chain carbon sources are particularly preferred. However, other suitable microorganisms (particularly including appropriately genetically modified microorganisms) such as yeast of other genera, such as Hansenula, Saccharomyces, Klyuveromyces, Debaromyces, Nadsonia, Lipomyces, Torulopsis, Kloeckera, Pichia, Schizosaccharomyces, Trigonopsis, Brettanomyces or Schwanniomyces may also be employed in some circumstances.

In accordance with various aspects of the present invention, the microorganisms utilized should be capable of utilizing ethanol as the principal carbon source in oxidative fermentation to carry out bioconversion of L-galactono-gamma-lactone to produce L-ascorbic acid in yields of at least about 1 gram per liter. However, the preferred microorganisms are mutants which belong to the genus Candida and which have the characteristics necessary for the production of L-ascorbic acid, further including characteristics such as transport of product into the bioconversion broth and enhanced ability to metabolize alcohol under aerobic conditions. However, in some instances, strains which accumulate significant amounts within the cell may be of value. Further, while ethanol is the particularly preferred carbon source, it is recognized that glycerol may serve as a fermentation carbon source for growth and/or production of L-ascorbic acid or other enediol compounds. The critical determinant for the selection of a carbon source is that it not be converted to an isomer of L-ascorbic acid. The yeast may be naturally occurring, artificially mutated or genetically engineered strains, particularly including those belonging to the genus Candida, provided they have the ability to produce and accumulate L-ascorbic acid.

Suitable mutants may be induced by conventional mutation procedures, such as exposure to ultraviolet (UV) rays, and/or chemical mutagens, such as N-methyl-N'-nitro-N-nitrosoguanidine, ethyl methane sulfonate, nitrous acid, acriflavin and caffeine. Hybridization of over-producing yeast strains using protoplast fusion or electrofusion to produce improved recombinants can be employed as can recombinant DNA technology. Further it is recognized that many genera of yeast can be induced to produce L-ascorbic acid or analogs under appropriate conditions. Such strains which are overproductive in ascorbic acid production may accumulate the bulk of the ascorbic acid within the cells so that it is not released until cellular autolysis occurs. However, for fermentation processes in which the L-ascorbic acid is most easily recovered from the fermentation medium, it is desirable for the microorganisms to transport the product into the medium.

Accordingly, a particular feature of the present disclosure is the provision of specific microorganism strains which do not retain the L-ascorbic acid product within the cell, but rather permit transport from the site of formation into the fermentation medium. It is believed that the enzymatic system which carries out the manufacture of L-ascorbic acid from the L-galactono-gamma-lactone substrate is associated with the yeast mitochondria. Accordingly, the L-galactono-gamma-lactone substrate must cross the cell wall from the fermentation medium, and further must be transported across the mitochondrial membrane. The L-ascorbic acid reaction product must similarly be transported across the mitochondrial membrane and the cell wall to enter the fermentation medium. To provide for accumulation of L-ascorbic acid in the fermentation medium, microorganism strains which have such desirable transport properties across the cell and mitochondrial membranes are provided. In this regard, particularly preferred embodiments of the present invention utilize selected yeast species and strains such as the Candida mutants described hereinafter, that transport the bulk of the L-ascorbic acid or analogs they produce into the fermentation medium during their tropophase and idiophase growth sequences. In accordance with the present invention, novel microorganisms are provided which are particularly adapted to aerobically oxidize an L-galactonic acid substrate, and particularly L-galactono-gamma-lactone, to produce therefrom and accumulate substantially only L-ascorbic acid. Particularly preferred are such microorganisms which have enhanced ability to metabolize ethanol under aerobic conditions and which transport L-ascorbic acid across cell and mitochondrial membranes so that the L-ascorbic acid is provided in the aqueous fermentation medium.

An example of a particularly preferred, artificially mutated yeast which produces and accumulates L-ascorbic acid when grown on an ethanol-containing standard fermentation medium ("SM-1") and a special glycine—containing medium ("glycine medium") each also containing 0.5% by weight L-galactono-gamma lactone, is *Candida norvegensis* Kraft, Inc. MF-56. This strain has been deposited with the American Type Culture Collection Rockville, Md. and has received culture identification ATCC 20686. Another, improved mutant strain is Candida norvegensis, Kraft, Inc. MF-78, which has been deposited with the American Type Culture Collection and has received culture identification number ATCC 20732. These yeasts are mutant strains derived and isolated through a series of mutagenic processes from *Candida norvegensis* CBS 2145.

The genealogy of the L-ascorbic acid over-producer MF-56 ATCC 20686, and L-ascorbic acid yields in both standard and glycine fermentation media, is provided in the following table.

TABLE I

Geneaology of L-Ascorbic Acid Over-Producers from *Candida norvegensis*

| Candida norvegensis | L-Ascorbic Acid Produced (grams/per liter) | |
|---|---|---|
| | SM-1 | Glycine Medium |
| CBS 2145$_{(EMS)}$ | 0.09 | 0.30 |
| MF-27$_{(UV)}$ | 0.015 | 0.60 |

TABLE I-continued

Geneaology of L-Ascorbic Acid Over-Producers from *Candida norvegensis*

| Candida norvegensis | L-Ascorbic Acid Produced (grams/per liter) | |
|---|---|---|
|  | SM-1 | Glycine Medium |
| MF-34$_{(UV/CAF)}$ | 0.020 | 0.72 |
| MF-39$_{(UV)}$ | 0.30 | 0.75 |
| MF-42$_{(NTG)}$ | 0.30 | 0.69 |
| MF-54$_{(NA)}$ | 0.33 | 0.75 |
| MF-55$_{(Ni+2)}$ | 0.34 | 0.80 |
| MF-56 | 0.34 | 1.07 |

Fermentations were carried out at 30° C. for 48 hours in low actinic 500 ml Erlenmeyer flasks containing 50 ml of the respective fermentation medium containing ethanol 1.5% w/v and L-galactono-gamma-lactone 0.5% (400 RPM). The mutation inducing or selective agents used to produce a subsequent strain from the previous strain is shown in parentheses, in accordance with the following abbreviations: UV=ultraviolet radiation; EMS=ethyl methane sulfonate; NTG=N-methyl-N'-nitro-N-nitrosoguanidine; NA=nitrous acid; CAF=caffeine; Ni$^{+2}$=Nickel L-galactonate.

The process of screening selection of over producing mutants for L-ascorbic acid may be carried out by applying mutagenic treatment to a large number of yeast cells, and subsequently selecting yeast colonies based on the level of ascorbic acid production. The level of ascorbic acid production may be monitored by culturing isolated cells of the mutagenicly treated yeast in a culture medium which is sensitive to acid production. For example, a culture medium may be opacified with an acid-sensitive material such as powdered calcium carbonate. Acid production by a growing yeast colony will dissolve the calcium carbonate, thereby providing a clarified zone surrounding the colony, the diameter of which increases as a function of increased yeast colony acid production.

Data for mutagenic treatment and screening in respect to one of the cultures in the geneology of Table I, designated as *C. norvegensis* MF-39 is set forth in the following Table II.

TABLE II

STRAIN SELECTION FOR L-ASCORBIC ACID PRODUCTION

| UV Exposure Time | Acid Units | | | | |
|---|---|---|---|---|---|
|  | 0–1.0 | 1.0–1.5 | 1.5–2.0 | 2.0–2.5 | 2.5 |
| 0 seconds (100% sur.) | 464/468 99.14% | 4/468 .85% | — | — | — |
| 15 seconds (13.66% sur.) | 300/313 95.84% | 8/313 2.5% | 5/313 1.59% | — | — |
| 30 seconds (4.8% sur.) | 4433/4480 83% | 27/4480 7% | 18/4480 9% | 2/4480 .88% | — |
| 45 seconds (.52% sur.) | 343/500 68.6% | 30/500 6% | 108/500 21.6% | 18/500 3.6% | 1/500 .20% |
| 60 seconds (.03% sur.) | 30/37 81.08% | — | 6/37 16.21% | 1/37 2.7% | — |
| 75 seconds (0.1% sur.) | 277/288 96.18% | 7/288 2.43% | 2/288 .69% | 1/288 .34% | 1/288 .34% |

In the work described by Table II, superior producing mutants were screened on the basis of their acid unitage (AU). In this regard, following mutagenic treatment the parent strain and the survivors were plated on an acid indicating medium, which was SM-1 culture medium containing Agar, ethanol 1.5% w/v, 0.5% L-galactono-gamma-lactone and mono-sodium glutamate 0.2%, further containing 0.3% Ca CO$_3$ as an opacifying agent, and incubated for 96 hours at 30° C. to determine their AU values. By AU values is meant the diameter of clear zone (mm)/diameter of colony zone. In Table II, the mutagenic U.V. exposure time is given in the first column of the table for exposure times of 0, 15, 30, 45, 60 and 75 seconds with the total survival percentage culture at that exposure time being shown thereunder. For each exposure time, the number fraction and percentage of surviving colonies are shown for each of the five different zone sizes of acid unitage, in respective columns of the table. Shake flask testing as described with respect to Table I is used for productivity evaluations. The MF-42 strain was selected from among the mutated strains having highest acid unitage.

As indicated, mutations and genealogical derivatives of strains which are productive in L-ascorbic acid may be provided and utilized in accordance with the present disclosure. In this regard, subsequent mutation of strain MF-56 (from Table I) is carried out to provide mutant strains which are even more overproductive in L-ascorbic acid, as set forth in the following table:

TABLE III

Geneaology of L-Ascorbic Acid Over-Producers From MF-56 ATCC 20686

| Candida norvegensis | L-Ascorbic Acid Produced (grams/per liter) |
|---|---|
| MF-56$_{(UV)}$ | 1.07 |
| MF-57$_{(UV/Vn + 2\,Res)}$ | 1.10 |
| MF-61$_{(UV)}$ | 1.30 |
| MF-61'$_{(Ce137)}$ | 1.31 |
| MF-64$_{(EtBr)}$ | 1.34 |
| MF-72$_{(UV)}$ | 1.38 |
| MF-77$_{(UV)}$ | 1.43 |
| MF-78 | 1.77 |

The mutation inducing or selecting agents utilized in producing the succeeding strain from the preceeding strain is shown in parentheses. Mutation or selection treatments are represented as follows: EMS=ethyl methane sulfonate; UV=ultra-violet irradiation, NTG=nitrosoguanidine, Ni+2=nickel salt complex; Ce-137=Cesium 137 gamma irradiation, EtBr=ethidium bromide; Na=nitrous acid; Vn+2=ammonium meta-vanadate. In Table III, the listed L-ascorbic acid production levels are obtained by shake flask fermentations as previously described in respect to Table I.

The morphological, cultural and physiological characteristics of the mutant strain *C. norvegensis* Kraft, Inc. MF-56 ATCC 20686, the mutant strain *C. norvegensis* Kraft, Inc. MF-78 ATCC 20732, and the parent strain *C. norvegensis* CBS 2145 are consistent with the yeast description provided in The Yeasts, a taxononomic study (J. Lodder (Ed.) 1970, North Holland Publishing Co., Amsterdam) and A New Key to the Yeasts (J. A. Barnett & R. J. Parkhurst (Ed) 1974, North Holland Publishing Co., Amsterdam). Morphological and identification tests are presented in Table IV.

When grown on malt extract at 25° C., cells are cylindrical to avoid (2–8)×(5–13) microns. Colonies are cream colored, glistening, soft and smooth. Ascospores are not formed on Folwells acetate agar.

TABLE IV

| Assimilation of carbon compounds: | | | |
|---|---|---|---|
| Glucose | + | Ethanol | + |
| Galactose | − | Methanol | − |
| L-Sorbose | − | Glycerol | + |

TABLE IV-continued

Assimilation of carbon compounds:

| | | | |
|---|---|---|---|
| Sucrose | − | Erythritol | − |
| Maltose | − | Ribitol | − |
| Cellobiose | + | Galactinol | − |
| Trehalose | − | D-Mannitol | − |
| Lactose | − | D-Glucitol | − |
| Melibiose | − | -Methyl-D-glucoside | − |
| Raffinose | − | Salicin | +/− |
| Melezitose | − | Arbutin | +/− |
| Insulin | − | DL-Lactic Acid | + |
| Soluble Starch | − | Succinic acid | + |
| D-Xylose + latent or | − | Citric acid | + |
| L-Arabinose | | Inositol | * |
| D-Arabinose | − | Glucono-delta-lactone | − |
| D-Ribose | − | 2-Keto-gluconate | − |
| L-Rhamnose | − | 5-Keto gluconate | − |
| | − | D-Glucosamine | + |

Assimilation of KNO₃: negative
Growth without added vitamins: negative; thiamine, biotin and pyridoxine are required
Maximum temperature for growth: 41–45° C.

*sometimes weak

Another feature of the present invention is provision of aqueous fermentation media and fermentation conditions under which metabolic processes of gluconeogenesis from ethanol may be repressed and formation of D-erythroascorbic acid may be minimized. Particularly preferred aqueous fermentation media may be provided which facilitate the recovery of L-ascorbic acid and which enhance the microbiological production of L-ascorbic acid. The provision of an appropriate aqueous fermentation medium is a further important feature of methods in accordance with the present invention, and selection and provision of a desired fermentation medium is in part a function of the particular microorganism utilized in the fermentation. The provision of an appropriate fermentation medium may also provide for more effective L-ascorbic acid recovery procedures by separation techniques including ion exchange resin separation methods, as will be discussed in more detail hereinafter.

Ethanol is used as the carbon source in the fermentation medium and the initial concentration is preferably in the range of about 0.01–2.0% weight (grams)/volume (milliliters) herein "w/v", depending upon the particular strain employed. As ethanol is consumed during the bioconversion it may be intermittently supplemented to give an optimum concentration (about 0.01%–2.0% w/v) which can be tolerated by the yeast and does not inhibit growth or L-ascorbic acid production.

In accordance with various aspects of such methods, an aqueous bioconversion medium is provided comprising a carbon fermentation energy source having less than four carbon atoms selected from the group comprising ethanol, glycerol and mixtures thereof, an L-galactonic substrate selected from the group consisting of L-galactono-gamma-lactone, L-galactonic acid, and mixtures thereof. The fermentation medium will generally further contain nutrients necessary for growth of the selected microorganism and will preferably have a pH in the range of from about 2.5 to about 6.5. Generally, at least about 0.01 weight percent, and preferably from about 0.1 to about 2.0 weight percent of the carbon source will be provided in the aqueous fermentation medium, based on the total weight of the fermentation medium. The carbon source is consumed during the fermentation and may be periodically or continuously added during the course of the fermentation. Similarly, at least about 0.1 weight percent of the fermentation substrate will desirably be provided in the fermentation medium based on the total weight of the medium. For yeast fermentations, the fermentation medium will generally include a nitrogen source, various organic nutrients, and various minerals.

The nitrogen source (which may typically be utilized in an amount of about 0.1 to about 0.5 weight percent based on the total weight of the aqueous fermentation medium) may be selected from the group metabolizable nitrogen compounds comprising ammonium sulfate, ammonium nitrate, ammonium chloride or ammonium phosphate, urea or ammonium ion in the form of ammonium hydroxide, etc. and mixtures thereof, depending on the ability of the particular strain to best utilize the nitrogen source. Further, various amounts of organic nutrients such as amino acids (e.g., monosodium glutamate, glutamine, aspartic acid, etc.) or purines (adenine, thymine) corn steep liquor, yeast extract, protein hydrolysates etc., inorganic salts, such as, sulfates or hydrochlorides of Ca, Mg, Na, K, Fe, Ni, Co., Cu, Mn, Mo, Zn; vitamins (e.g., water soluble B vitamins) may be added to prepare a culture or fermentation medium. One such medium which effectively carries out this function is the previously referred to SM-1 ethanol medium. The compositional characteristics of this medium are listed as follows:

| | SM-1 MEDIUM | |
|---|---|---|
| | | Amount |
| | | G.L.$^{-1}$ |
| A. | carbon - ethanol (weight/volume) | 15.0 |
| B. | nitrogen - urea | 2.0 |
| C. | Supp mix - corn steep liquor | 5.0 |
| D. | Inorganic | |
| | Salts - K$_2$HPO$_4$.3H$_2$O | 1.0 |
| | KH$_2$PO$_4$ | 3.0 |
| | MgSO$_4$.7H$_2$O | 0.5 |
| | NaCl | 0.1 |
| | KCl | 0.1 |
| | H$_3$BO$_3$ | .0005 |
| | FeCl$_3$.6H$_2$O | .0002 |
| | MnSO$_4$H$_2$O | .0004 |
| | ZuSo$_4$.5H$_2$O | .0004 |
| | CUSO$_4$.5H$_2$O | .0004 |
| | KI | .0001 |
| | (NH$_4$)$_6$MO$_7$O$_{24}$.4H$_2$O | .0002 |
| E. | Vitamins - Thiamine HCl | .004 |
| | Biotin | .00002 |
| F. | Bioconversion Compd. L-galactono-δ-Lactone | 5.0 |
| G. | Adjust to pH 4.0 | |

When selected mutant yeast are grown in this medium under appropriate cultural conditions essentially only L-ascorbic acid is produced as the bioconversion product of L-galactono-gamma-lactone provided in the culture medium. Modifications of this medium or other media (as will be more fully discussed hereinafter) may prove to be more beneficial. The conditions for culturing are typically a temperature in the range of from about 20° C. to about 37° C. and preferably about 30° C. The bioconversion is desirably carried out at a pH in the range of from about 6.5 to about 2.6 and preferably about 4.0. The optimum conditions will depend on the particular yeast strain employed. The fermentation process may take from 1 to 7 days and is operated under aerobic conditions. When a high density yeast cell biomass (range 25–240 grams of wet cells per liter of bioconversion medium) is employed in the bioconversion process to produce L-ascorbic acid, the additional supplementation of pure oxygen or an oxygen enriched atmosphere to the aeration process may be required to prevent the development of anaerobic conditions or may be desirable to enhance yields. It is desirable that at least about 2.5 ppm oxygen be maintained in the aqueous culture medium, and preferably the oxygen content should not decrease below a predetermined level in the range of from about 3 to about 5 ppm.

While standard culture media such as the SM-1 culture medium previously described may advantageously be utilized in the manufacture of L-ascorbic acid from a L-galactono-gamma-lactone substrate in accordance with the present invention, it is particularly preferred that all growth or fermentation be carried out utilizing a culture medium of at least about 0.5 weight percent and preferably in the range of from about 0.6 weight percent to about 0.8 weight percent glycine, based on the total weight of the culture medium. It has been found that about 0.7 weight percent glycine in the medium is particularly effective in respect to yield enhancement. In this regard, it has been found that such high glycine culture media appear to enhance the yield productivity of L-ascorbic acid by factors of about 3 or more. The components of a glycine fermentation medium which has proven to be particularly effective in the fermentations described herein, and which are identified herein as "glycine medium" are listed as follows:

| GLYCINE MEDIUM | |
|---|---|
| component | amount (grams per liter) |
| Ethanol | 20.0 |
| Glycine | 7.0 |
| CSL w/v | 5.0 |
| mono sodium glutamate | 2.0 |
| NH$_4$Cl | 1.0 |
| Mg SO$_4$ | 0.5 |
| mineral mix | 2.0 ml |
| The mineral mix consists of: | |
| EDTA (2Na) | 5.0 grams per liter |
| ZnSO$_4$.7H$_2$O | 0.22 grams per liter |
| CaCl$_2$.2H$_2$O | 0.735 grams per liter |
| MnSO$_4$.H$_2$O | 0.6725 grams per liter |
| FeSO$_4$.7H$_2$O | 0.915 grams per liter |
| (NH$_4$)$_6$ Mo$_7$O$_{24}$ · 4H$_2$O | 0.10 grams per liter |
| CuSO$_4$.5H$_2$O | 0.25 grams per liter |
| CoCl$_2$.6H$_2$O | 0.293 grams per liter |

High glycine medium may be provided for commercial scale operations by hydrolyzing proteins such as gelatin having a high glycine content, and directly utilizing the hydrolysis products in the fermentation of the growth medium for the ascorbic acid overproducing microorganism.

As will be more fully described, the L-galactonic substrate may desirably be manufactured from cheese or dairy byproduct lactose by hydrolyzing the lactose to produce glucose and D-galactose and oxidizing the D-galactose to produce D-galacturonic acid:

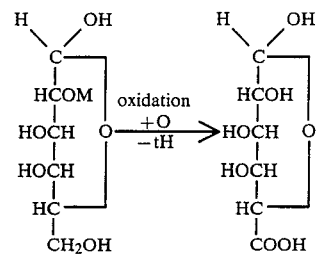

D-galacturonic acid may also conveniently be provided by hydrolysis, such as enzymatic hydrolysis, of pectinaceous materials such as citrus pectin. The D-galacturonic acid may be reduced to provide L-galactonic acid, which may be dehydrated to form L-galactano-gamma-lactone:

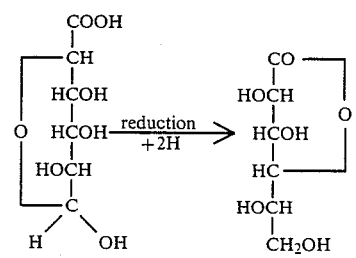

Various derivatives of L-galactonic acid particularly including the lower alkyl esters may be manufactured by conventional esterification reaction of L-galactonic acid:

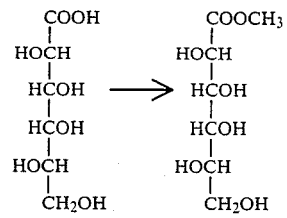

In particularly preferred bioconversion processes, the growth of the overproducing microorganism to produce cell biomass is conducted as a first stage fermentation in a suitable growth medium with the presence of an L-galactonic substrate to produce a cell mass for subsequent bioconversion utilization. Desirably, the growth medium will have a high glycine content of at least about 0.02% w/v (grams per 100 milliliters), as discussed herein. Because the first stage fermentation is not directly carried out for L-ascorbic acid production, the growth fermentation medium also need not contain ethanol, and may utilize a conventional and readily available carbon source such as glucose. The cell biomass from the first stage growth fermentation system, which is preferably formulated to maximize cell growth, may be collected and utilized to provide a high cell density bioconversion medium which need not be formulated to maximize cell growth. The high cell density bioconversion medium will desirably contain at least about 5.0 grams dry cell weight and preferably from about 25 grams to about 100 grams dry cell weight per liter of the ascorbic acid overproducing microorganisms. The bioconversion reaction may be carried out to produce high L-ascorbic acid concentrations by providing the ethanol carbon source and L-galactonic substrate in such high cell density systems.

In carrying out the bioconversion, aerobic conditions are maintained under which the substrate is oxidized by the microorganism to substantially only L-ascorbic acid produced by the microbiological oxidation. The L-ascorbic acid produced by the aerobic fermentation may be subsequently recovered in an appropriate manner, as will be more fully described.

It is necessary to maintain aerobic conditions during the bioconversion, and in this regard, it is desirable that at least 20% (e.g., 20-30% oxygen-saturation (e.g., 2-3 ppm of oxygen) be maintained in the aqueous fermentation medium during the fermentation. Maintaining aerobic conditions may be carried out by introducing oxygen enriched gas into the fermentation medium, and by utilizing fermentation equipment, such as air lift reactors, which effectively disperse oxygen into the fermentation medium.

As indicated, ethanol may be utilized as the principal carbon energy source under bioconversion conditions in which L-galactono-gamma-lactone is substantially wholly converted to L-ascorbic acid. For example, when Candida yeast are grown on ethanol (a 2-carbon energy source), employing SM-1 medium and 0.5 weight percent L-galactano-gamma-lactone rather than on hexose sugar (6-carbon energy source) as the energy source in SM-1 medium with 0.5% L-galactono gamma-lactone essentially only L-ascorbic acid is formed and production of other ascorbic acid analogs, e.g., D-erythroascorbic acid is minimized. This is an important factor in the development of a practical process to produce L-ascorbic acid at levels of industrial interest.

In the bioconversion process, L-galactono-gamma-lactone is converted to a structually related product by one or a small number of enzymes within a cell. The process may be carried out using growing cells, resting vegetative cells, dried cells or cells immobilized in various organic polymers, such as K-carrageenan, sodium alginate, polyacrylamide, gelatin, or agar, or other macroporous resins or inorganic compounds, such as cordierite and silica. Cell mitochondria containing the active enzyme may also be isolated and immobilized in order to carry out a bioconversion.

The L-ascorbic acid bioconversion process may be operated in conventional aerobic fermentation modes, e.g., batch, continuous, semi-continuous. Also cultivation methods usable to obtain high-density of biomass; dialysis culture, semi-batch with cell separator and fed-batch processes may be employed in which oxygen supplements to air may be required.

Having generally described the present invention, various aspects thereof will now be more particularly described with respect to the process embodiment illustrated in block diagram by FIG. 1.

FIG. 1 is a schematic illustration of an embodiment of a process for manufacturing L-ascorbic acid from a dairy by product lactose solution substrate 10 such as whey, whey permeate or milk permeate. The dairy fluid lactose solution may typically comprise from about 4.5 to about 5.0 weight percent lactose, which is hydrolyzed to provide its constituent sugars, glucose and galactose in the form of glucose-galactose solution 12. The hydrolysis may be accomplished in a conventional manner using a lactase enzyme derived from a yeast (*K. fragilis* or *K. lactis*) or a mold enzyme derived from *A. niger* or *A. oryzae*. The enzyme may be employed either in a free, entrapped or immobilized form.

The glucose-galactose solution 12 or the lactose solution 10 may be deproteinized or demineralized in accordance with conventional procedures if necessary or desirable in carrying out the alcohol fermentation. The glucose-galactose solution provided by the hydrolysis treatment step may be concentrated to provide a solution comprising for example in the range of from about 15 percent to about 30 percent by weight, based on the total weight in the solids solution. The non-lactose solids content may typically be in the range of from about 0.5 to about 1.0 weight percent of the total solids, such that the total glucose and galactose content of the solution may desirably be in the range of from about 20.0 to about 22.5 percent by weight based on the total weight of the solution.

After supplementation with suitable nutrients such corn steep liquor or yeast extract in accordance with conventional yeast fermentation procedures, the glucose-galactose solution 12 may be fermented under anaerobic conditions using an appropriate yeast strain for fermentation of glucose to ethanol, such as a selected yeast strain of *S. cerevisiae*, in order to convert the glucose to ethanol and carbon dioxide without substantially consuming the galactose component of the fermentation medium. In this manner an ethanol-galactose solution 14 is provided.

The ethanl-galactose fermentate may typically comprise at least about 5 percent ethanol on a weight to volume basis, and at least about 10 weight percent D-galactose based on the volume and weight of the fermentation 14 respectively. The fermentate 14 is distilled to remove the alcohol 16 which may subsequently be rectified to provide 190 proof ethyl alcohol, if desired. This alcohol 16 may then be utilized in the L-ascorbic acid fermentation process to serve as carbon energy for the selected microorganism utilized in the fermentation.

In this regard, the stillage containing D-galactose recovered after removal of ethanol may be concentrated further by appropriate methods to provide a galactose solution having a total solids content in the range of from about 20 to about 75 weight percent based on the total weight of the solution, and which may desirably contain from about 16 to about 62 weight percent of galactose based on total solution weight. This galactose solution may be crystallized to obtain purified D-galactose 18. The mineral salts 20 may be utilized in the L-ascorbic acid fermentation, if desired; as a supply of inorganic nutrients for the fermentation medium. Alternatively the galactose may be separated from the rest of the fermentation components via ion exclusion. Such galactose can serve directly as the feedstock for reaction step 18.

The D-galactose 18 is converted by catalytic oxidation to provide D-galacturonic acid 22. Processes to carry out this oxidative step for D-sugar acids are well known in the art and have been described in U.S. Pat. No. 2,265,121 by T. Reichstein. A variety of catalytic agents, e.g., platinum or palladium catalysts may be employed to convert blocked D-galactose (acetone) to the D-galacturonic acid product. The unblocked D-galacturonic acid may then be reduced by an appropriate reduction step such as reduction with gaseous hydrogen in the presence of a suitable hydrogenation catalyst such as Raney nickel, or palladium, to produce L-galactonic acid 24. Processes to carry out this chemical reduction are well known in the art such as described by H. Isbell, *J. Res. Nat. Bur. Stds., 33,* 45–60 (1944). Removal of water by distillation and condensation of the desalted L-sugar acid induces the formation of L-galactono-gamma-lactone 26 which is utilized in the microbiological conversion process of the present invention to form L-ascorbic acid. Other galactose derivatives such as L-galactonic acid esters and L-galactonic acid may be utilized although yields of L-ascorbic acid are reduced due to less efficient utilization. Keto-derivatives such as 5-Keto-L-Galactonic acid, are not utilized by the preferred yeast strains particularly described herein. The L-galactono-gamma-lactone 26, ethanol 16, and suitable organic and inorganic nutrients are combined to provide a fermentation medium 28 for a selected L-ascorbic acid overproducer.

The L-ascorbic acid fermentation process may be carried out in conventional stirred aerated fermentors such as a 30 liter New Brunswick Scientific fermenter. Monitoring of product formation and control of the cellular environment using physical and chemical sensors linked to a microcomputer may be carried out by means of detectors for measuring ethanol, pressure, an input flow, exhaust gas, carbon dioxide, exhaust gas oxygen, pH, and dissolved oxygen.

After cultivation, L-ascorbic acid 30 produced by the fermentation may be recovered from the clarified fermentation broth by a variety of methods such as by using ion exchange resins, absorption or ion retardation resins, activated carbon, concentration-crystallization, etc.

The course of the fermentation may be monitored by appropriate analytical procedure. Quantitative assay of L-ascorbic acid and analogs may be carried out using redox-titration with 2,6 dichloroindophenol [N.G. Burton, et al., *J. Assoc. Pub. Analysts, 17,* 105 (1979)] and high-performance liquid chromatography [*J. Chrom.,* 196, 163 (1980)] and electro-redox procedures. [L.A. Pachia, *Anal. Chem.,* 48, 364 (1976)]. Enzymatic procedures involving the use of ascorbic acid oxidase (Boehringer-Mannheim) may also be employed.

The fermentation may be terminated when maximal production of L-ascorbic acid has been attained in the fermentation broth. Unconverted portions of L-galactono-gamma-lactone may be recycled.

Various aspects of the present invention will be further described with respect to the following specific examples, which are not intended to limit the scope of the invention.

EXAMPLE I

A stirred batch fermentation to produce L-ascorbic acid was carried out in a 30-Liter New Brunswick stirred fermentor. Fifteen liters of glycine medium composed of 0.25% corn steep liquor, 0.1% ammonium chloride, 0.7% glycine, 0.05% magnesium sulfate. $7H_2O$, 0.2% monosodium glutamate, 1.5% w/v ethanol and 0.30 ml of trace mineral mixture, was adjusted to pH 4.2 and sterilized for 30 minutes at 121° C. (Unless otherwise indicated values herein are in weight percentages). After cooling, 0.5% of cold-sterilized L-galactono-gamma-lactone was added to the sterile fermentation broth. The fermentor was inoculated with 500 ml of a 24 hour SM-1 broth culture of *C. norvegensis* KCC MF42 (Table I) grown in a 2-liter Erlenmeyer flask on a rotary shaker at 30° C., 200 RPM.

The fermentor was operated at 30° C., 250 RPM and an aeration rate of 0.25 vol/vol/min. with the pH initially maintained at 4.0. After 24 hours, the supernatant broth contained 0.084 grams per liter ($gL^{-1}$) of L-ascorbic acid. An additional 27.0 mg was present in the yeast cells. After 48 hours the clarified broth contained 0.43 $gL^{-1}$ of L-ascorbic acid and the cells contained 29.6 mg. $L^{-1}$. The product could be recovered using conventional ion exchange resin absorption and elution followed by decolorization, evaporation and crystallization.

EXAMPLE II

A system of process intensification using high density biomass and product recovery was developed for the production of L-ascorbic acid using Candida yeast and mutants. In this procedure KCC MF-42 yeast cells were cultivated in SM-1 medium (ETOH 1.5% w/v) (L-Galactono-gamma-lactone 0.1%) for 18 hours in a stirred fermentor and centrifuged under sterile conditions. The cell paste provided by centrifugation was then aseptically reconstituted at 37.5 g $L^{-1}$ wet cell weight in sterile fresh SM-1 medium, pH 4.0 (Ethanol 1.5%—monosodium glutamate 0.2%—L-galactono-gamma-lactone 0.5%) and aerated with oxygen at a dissolved oxygen level of 65% of saturation. Production of L-ascorbic acid rose to 0.470 $gL^{-1}$ in 24 hours and increased to 0.580 $gL^{-1}$ in 45 hours. The pH of the medium dropped to 2.6 during the fermentation. L Four liters of chilled, clarified fermentation broth were passed through a 500 ml column of IR120 ($H^+$) resin, an ion exchange resin manufactured by Rohm & Haas. The effluent and washwater were collected and evaporated to 100 ml volume at 37° C. under vacuum. One hundred milliliters of cold ethanol was added and the precipitate (protein) was removed by centrifugation at 5000 RPM at 5° C. The product was again evaporated to 25 ml volume and stored at 0° C. for five days until crystallization was complete. The filtered crystals were washed 3 times with acetone, redissolved in warm alcohol and recrystallized. About 1.4 g of crude L-ascorbic acid crystals (HPLC) were recovered in the first crop.

Recovery and purification can also be carried out by absorption of L-ascorbic acid from broth on anion retardation resin (Dowex 1 type), acetate form and elution with 0.1 M $H_2SO_4$.

EXAMPLE III

A process was developed in which resting cells of Candida yeast and mutants were used to produce L-ascorbic acid from ethanol and L-galactono-gamma-lactone in buffered salt solution. Both ethanol and L-sugar lactone are required by the yeast. The resulting cells may be used in a free state or immobilized in various polymeric gels or attached to polymeric resins, or inorganic mineral compounds.

In this example, yeast cells *Candida norvegensis* CBS #1911 cultivated 18 hours in SM-1 medium were centrifuged, washed in phosphate buffer (pH 4.5) and resuspended at a level of 3.0 grams wet cell weight/50 ml of 0.03% phosphate buffer solution (pH 4.5) containing 0.8% ethanol and 0.5% L-galactono-gamma-lactone. The 50 ml mixture in a 500 milliliter low-actinic, borosilicate Erlenmeyer flask was placed on a rotary shaker and aerated at 300 RPM at 30° C. Broth samples were taken periodically in order to monitor ethanol utilization and L-ascorbic acid production. Additions of ethanol were made periodically to maintain the alcohol concentration at about 0.3% w/v concentration. Results of the L-ascorbic acid accumulation by the yeast after 96 hours are shown in TABLE V:

TABLE V

| Microorganism used C. Norvegensis CBS - #1911 | L-ascorbic acid accumulated micrograms per liter | Time Hours |
|---|---|---|
| | 90 | 33 |
| | 130 | 48 |
| | 200 | 73 |
| | 260 | 96 |

EXAMPLE IV

A screening program was initiated for the selection of microorganisms capable of converting galactose derivatives and preferably L-galactono-gamma-lactone to L-ascorbic acid. Microorganisms of the genus Candida were selected from the varieties of yeast reported capable of producing enediol compounds.

A large number of Candida species readily available in various culture collections, e.g., American Type Culture Collection, Rockville, Md., Central-Bureau voor Schimmelculture, Delft, Institute Pasteur, Paris and Northern Region Research Lab, Peoria, Ill., were accessed and purified prior to screening studies. The cultures were maintained on G-agar slant tubes or other nutrient media.

A saline suspension of a 24 hour slant of yeast grown on G-agar was employed as the inoculum. A 0.5 ml cell suspension was aseptically added to 50 ml of sterile SM-1 medium (ethanol 1.5% w/v, urea 0.2%) in a 500 ml low actinic Erlenmeyer flask. L-galactano-gamma-lactone (0.5%) was cold sterilized and added to the cooled flasks. The flasks were placed on a rotary shaker and aerated at 200 rpm, 30° C. for 48 hours. The clarified broths were examined for L-ascorbic acid production. The centrifuged, washed cell pastes were treated with 3.0 ml of 10% trichloracetic acid and titrated with 2,6, dichloroindophenol to establish the level of reducing compounds present within the cell. Conversion of L-galactono-gamma-lactone to L-ascorbic acid was observed in the following species, as shown by Table VI.

TABLE VI

| | | Production of L-Ascorbic Acid ($L-AAH_2$) | | | |
|---|---|---|---|---|---|
| | | | Micrograms per deciliter | | |
| Organism | Source | No # | Broth | Cells | Total |
| C. ingens | CBS | 4603 | 350 | 3717 | 4067 |
| C. truncata | CBS | 1899 | 2730 | 5691 | 8421 |
| C. lusitaniae | CBS | 4413 | 1820 | 2100 | 3920 |
| C. berthetii | ATCC | 18808 | 1330 | 2394 | 3724 |
| C. maltusa | ATCC | 20184 | 630 | 1470 | 2100 |
| C. langeronii | ATCC | 22972 | 910 | 1386 | 2296 |
| C. parapsilosis | ATCC | 22019 | 140 | 462 | 602 |
| C. maltosa | ATCC | 28140 | 560 | 1764 | 2324 |
| C. silvae | ATCC | 22685 | 70 | 168 | 238 |
| C. reukaufii | CBS | 611 | 0 | 147 | 147 |
| C. utiliis | NRRL | Y-900 | 9660 | 7581 | 17241 |
| H. anomala | ATCC | 20029 | 1610 | 2961 | 4571 |
| C. utilis | ATCC | 15239 | 11970 | 3402 | 15372 |
| Y. lipolytica | ATCC | 20390 | 280 | 3696 | 3976 |
| Y. lipolytica | ATCC | 8661 | 70 | 3465 | 3535 |
| C. guilliermondii | IP | 47 | 1820 | 798 | 2618 |
| C. zeylanoides | IP | 207 | 0 | 168 | 168 |
| C. pseudotropicalis | IP | 513 | 70 | 168 | 238 |
| C. pelliculosa | IP | 606 | 1750 | 420 | 2170 |
| C. pulcherrima | IP | 622 | 420 | 756 | 1176 |
| C. robusta | IP | 826 | 0 | 231 | 231 |
| T. candida | ATCC | 10539 | 280 | 546 | 826 |
| C. sloofii | ATCC | 22978 | 0 | 147 | 147 |
| C. norvegensis | CBS | 1911 | 10780 | 1113 | 11893 |
| C. amyloanta | NRRL | Y-7784 | 140 | 168 | 308 |
| C. buinensis | NRRL | Y-11706 | 0 | 147 | 147 |
| C. cacaoi | NRRL | Y-7302 | 1960 | 1428 | 3388 |
| C. conglobata | NRRL | Y-1504 | 0 | 147 | 147 |
| C. deformans | NRRL | Y-321 | 70 | 168 | 238 |
| F. fluviotilis | NRRL | Y-7711 | 420 | 546 | 966 |
| C. vinii | NRRL | Y-94 | 4130 | 2520 | 6650 |

EXAMPLE V

Airlift fermentors have several distinct advantages over conventional agitator-driven shaft fermentors. Among these are improved mass transfer of oxygen, reduced power requirements, and a more gentle environment for the cultivation of organisms compared to the high degree of shear present in mechanically agitated fermentors. Because of these features, airlift fermentors are desirably employed on an industrial scale. The following examples illustrate the use of an airlift tower fermentor for the production of Vitamin C using Candida yeast.

A 4.0 liter laboratory scale airlift fermentor was filled with sterile glycine medium, pH 4.1, containing 2.75% w/v ethanol, 0.7% glycine and 0.5% L-galactono-gamma-lactone. The fermentor was inoculated with a 24 hour suspension of the C. norvegensis KCC MF-42 cells washed from G-Agar (2.5%) flasks. The viable cell count at 0 hour was $5.5 \times 10^6$. Aeration of the fermentor was adjusted to 1.9 liters of air per liter of fermentation medium per minute [V/V/minute] which provided a cycle rate of 5.0 $m^{-1}$. After 24 hours at 30° C., the viable cell count rose to $1.1 \times 10^8$, and at 48 hours was $3.0 \times 10^8$, at 72 hours the viable cell count was $2.8 \times 10^8$. The count declined to $1.7 \times 10^8$ after 91 hours of cultivation. A level of 0.72 $gL^{-1}$ of L-ascorbic acid was produced.

EXAMPLE VI

In a similar airlift tower experiment a high cell density fermentation was performed. In this instance a 24 hour wet cell paste of C. norvegensis KCC MF-42 was dispersed in the 4.0 liter tower at a level of 100 $gL^{-1}$ in SM-1 medium containing 0.7% glycine and 0.7% L-Galactono-gamma-lactone. Ethanol was supplied continuously at a level (0.1–0.3%) neither limiting or inhibitory to yeast growth or productivity. Oxygen-enriched aeration was supplied to the fermentor at 1:1 oxygen-air ratio. Total mixed gas volume was 1.7 V/V/min. Under these conditions a dissolved oxygen saturation level of 30% was maintained in the upper section of the tower. After 20 hours of fermentation, L-ascorbic acid was produced at a level of 1.44 $gL^{-1}$.

EXAMPLE VII

This example illustrates the manufacture of L-ascorbic acid utilizing high cell density bioconversion conditions. A mutant strain of Candida norvegensis MF-78 Kraft, Inc. ATCC 20732, and having the genealogy presented in Tables I and III was cultivated at 30° C. on G-Agar slants (glucose 0.5%, trypticase-peptone 0.2%, yeast extract 0.5%, agar 1.5%) for 24 hours. Washed cells from 6 slants were used to inoculate 20 liters of sterile SM-1 glucose medium (glucose 1.5%, corn steep liquor 0.5%, sodium glutamate 0.2%, ammonium chloride 0.1%, glycine 0.02%, delactosed whey permeate 0.1%, $MgSO_4.7H_2O$ 0.05%, L-galactono-1,4,lactone 0.02%) in a 30 liter stainless steel fermentor. The cells were cultured at 30° C., 200 rpm, and aerated at 0.5 liter V/V/min for 24 hours.

The yeast inoculum (20 L) was transferred under sterile conditions to a 750 L stainless steel Chemap fermentor containing 492 L of sterile SM-1 glucose medium in order to carry out a first stage yeast biomass fermentation to generate cell mass for a subsequent high cell density bioconversion. The fermentation conditions were 30° C., the agitation rate was 200 rpm, and the aeration rate was 0.5 L V/V/min. The pH of the medium was initially adjusted to 4.0 and then allowed to drop to 2.6 during the growth phase. After 17 hours of fermentation, the culture broth was chilled to 4° C. and the cells were recovered by centrifugation. Yeast growth was monitored by dry cell weight, optical density (OD) 660nm, and total colony plate counts on Standard Plate Count Agar (Oxoid). An average yield of 10.82 kg of cell paste was obtained. Yield of cell paste from yeast grown on ethanol as carbon substrate were essentially the same. These cells were employed in the second stage bioconversion process for L-Ascorbic acid production.

The bioconversion process for converting L-galactono-1,4-lactone to L-ascorbic acid was carried out in 7.5 L New Brunswick glass fermentors containing 5.0 L of sterile glycine (0.7% w/v) medium with 0.1% w/v delactosed whey permeate. Supplements of cold sterilized added. One hundred fifty grams of chilled wet cell paste (C. norvegensis KCC MF-78) per liter of medium was then added aseptically to the sterile medium at pH 5.2. The dissolved oxygen tension was maintained near 30% using oxygen supplemented air monitored by New Brunswick membrane probes. Agitation was set at 350 rpm and the temperature was held at 28° C. for the duration of the conversion reaction. During the production process the ethanol level was allowed to drop to 0.2% w/v and was then periodically supplemented to maintain levels in the range of 0.2–0.5%. The level of L-galactono-1,4-lactone was maintained in the range of 1.2–1.5% by substrate additions at 4–8 hour intervals.

Production of L-ascorbic acid was monitored continuously by HPLC analysis using Aminex HPX-85 resin with an LC-4B amperometric probe. Values were checked at frequent intervals by redox dye titration using 2,6 dichloro-indophenol.

Results of the bioconversion process indicate that after an initial 2 hour lag period an L-ascorbic acid productivity rate of 0.32 grams per liter per hour (g/L/h) was attained. After 10 hours the rate gradually declined to 0.20 g/L/h (10 hours) and then to 0.15 g/L/h for the final 16 hour period. Final yield of L-ascorbic acid was 7.35 g/L in the supernatant broth. Lysis of yeast cells present in the broth by the addition of sodium dodecyl sulfate (SDS) at 1 mg/mL increased the final titer to 7.51 g/L.

EXAMPLE VIII

Two pounds of Red Star baker's yeast (Saccharomyces Cerevisiae), which is not overproductive in L-Ascorbic acid were disrupted according to the method of Tzagoloff [J. Biol. Chem., 244, 5020 (1969)]. The frozen powder (900 gm) was transferred to 1.5l of a solution consisting of 0.4 M sucrose, 0.05 M Tris(hydroxymethyl) amino methane (Tris-HCl) pH 8.2, with one millimolar ethylene diamine tetracetic acid (EDTA). The pH of the suspension was adjusted to 7.5 with sodium hydroxide and the suspension was subsequently homogenized in a blender for 45 seconds. The homogenate was centrifuged at 2500×g for 15 minutes at 4° C. and the cell debris was discarded. The supernatant was centrifuged at 62000×g in a Shar-les centrifuge. The pellet (mitochondria) was saved and resuspended in 250 ml of a solution containing 0.25 M sucrose and 0.01 M Tris-HCl pH 7.5 and frozen.

An assay mixture is provided which contains 2mM L-galactono-1,4-lactone and 50 mM Na-Citrate pH 6.8 in a total volume of 3 ml. The mixture is incubated at 37° C. in a shaker bath for up to 30 minutes. The reaction is stopped by adding 0.3 ml of 50% TCA. The precipitated protein is removed by centrifugation and the supernatant is assayed for L-ascorbate by high performance liquid chromatography analysis with electrochemical detection and by 2,6,dichloroindophenol titration.

Figure 2:
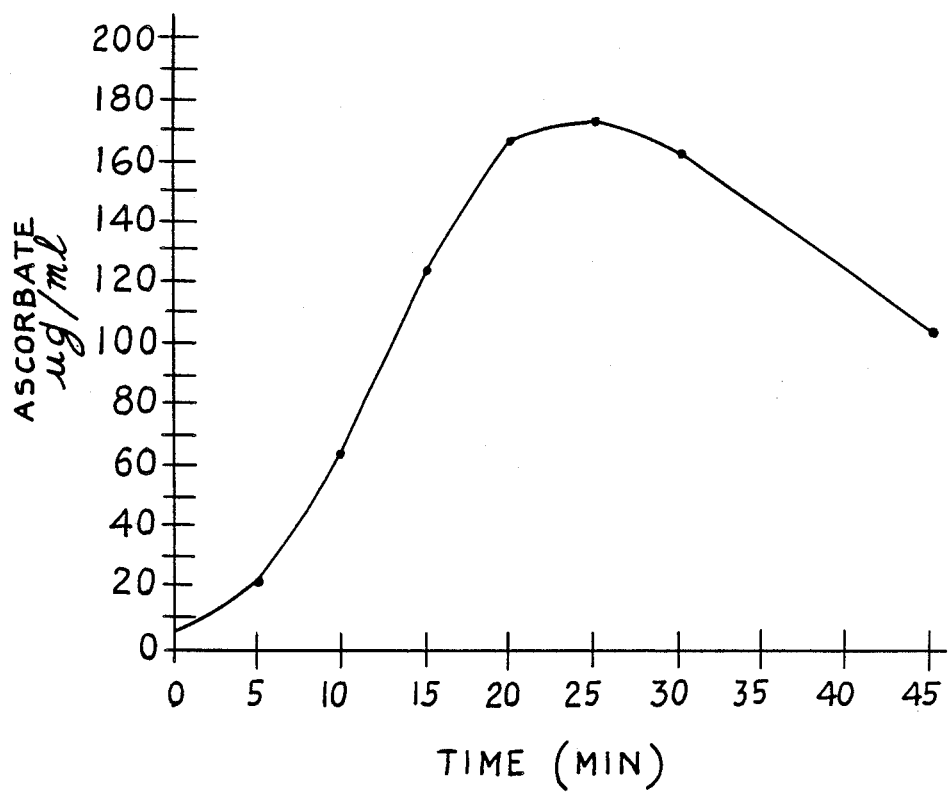
FIG. 2 is a graphic representation of a mitochondrial assay for L-galactono, 1,4-lactone oxidase activity.
Figure 3:
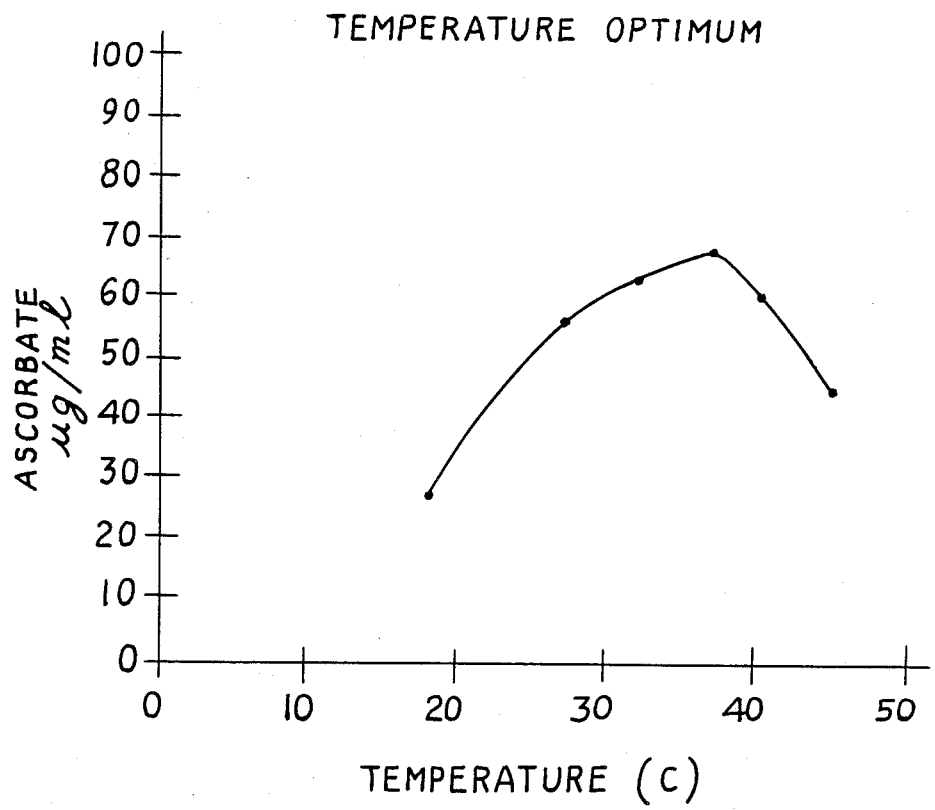
FIG. 3 is a graphic representation of mitochondrial ascorbate production from L-galactono-1,4-lactone as a function of temperature.
Figure 4:
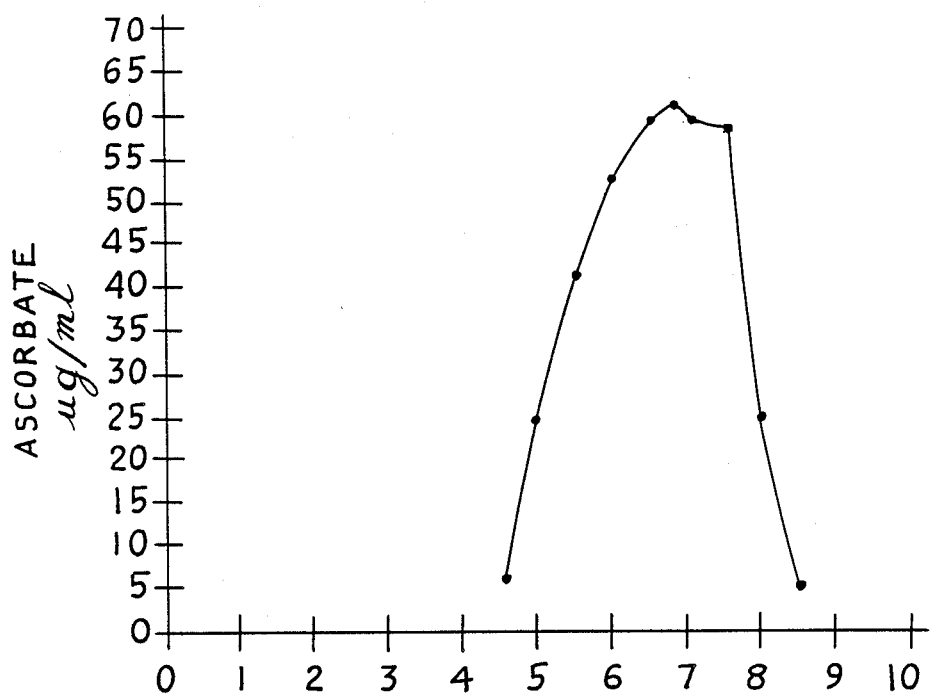
FIG. 4 is a graphic representation of mitochondrial ascorbate production from L-galactono-1,4-lactone as a function of pH.
Figure 5:
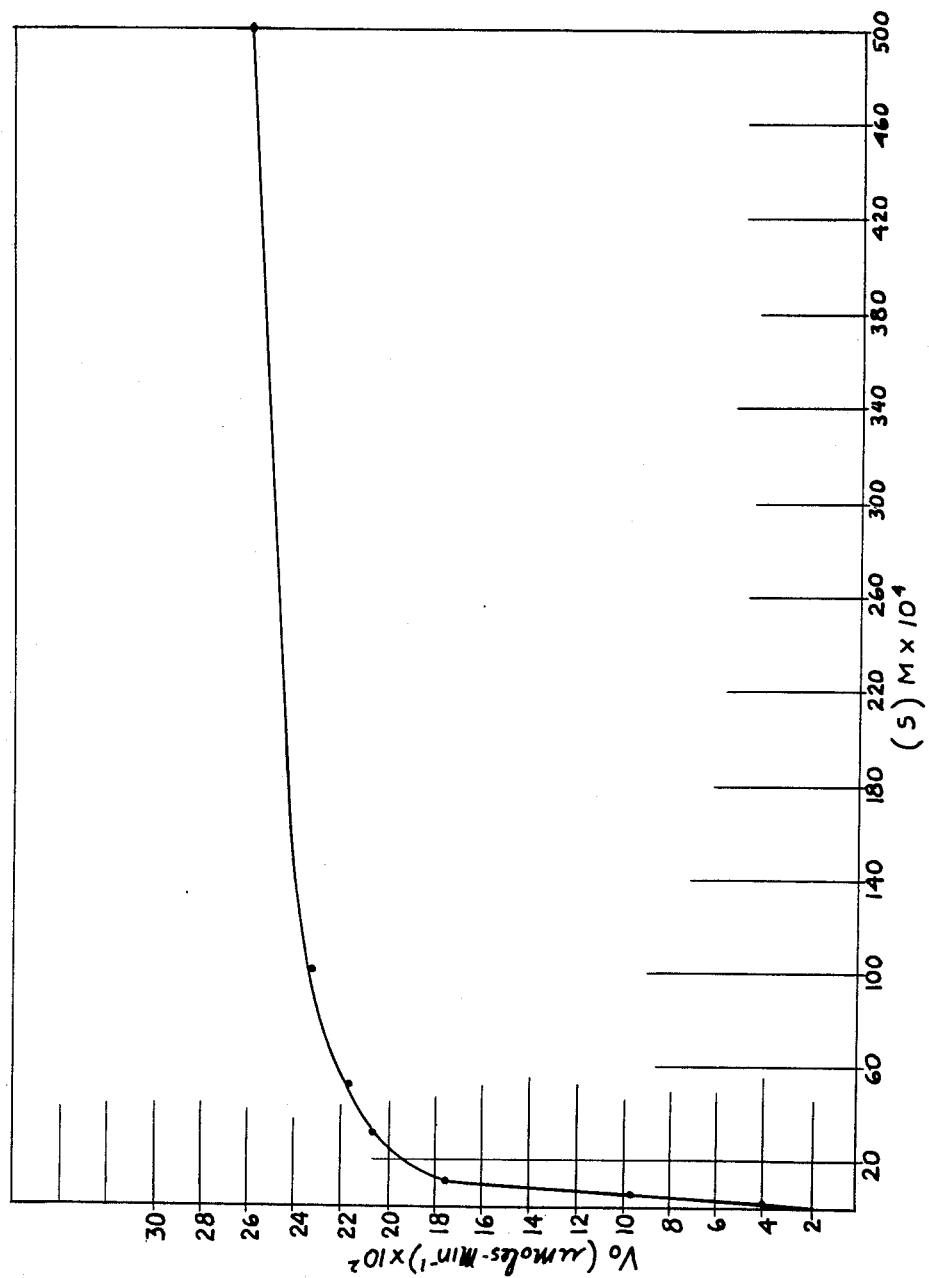
FIG. 5 is a graphic representation of mitochondrial reaction velocity $V_o$ for L-ascorbic acid versus concentration of L-galactono-1,4-lactone substrate.
Figure 6:
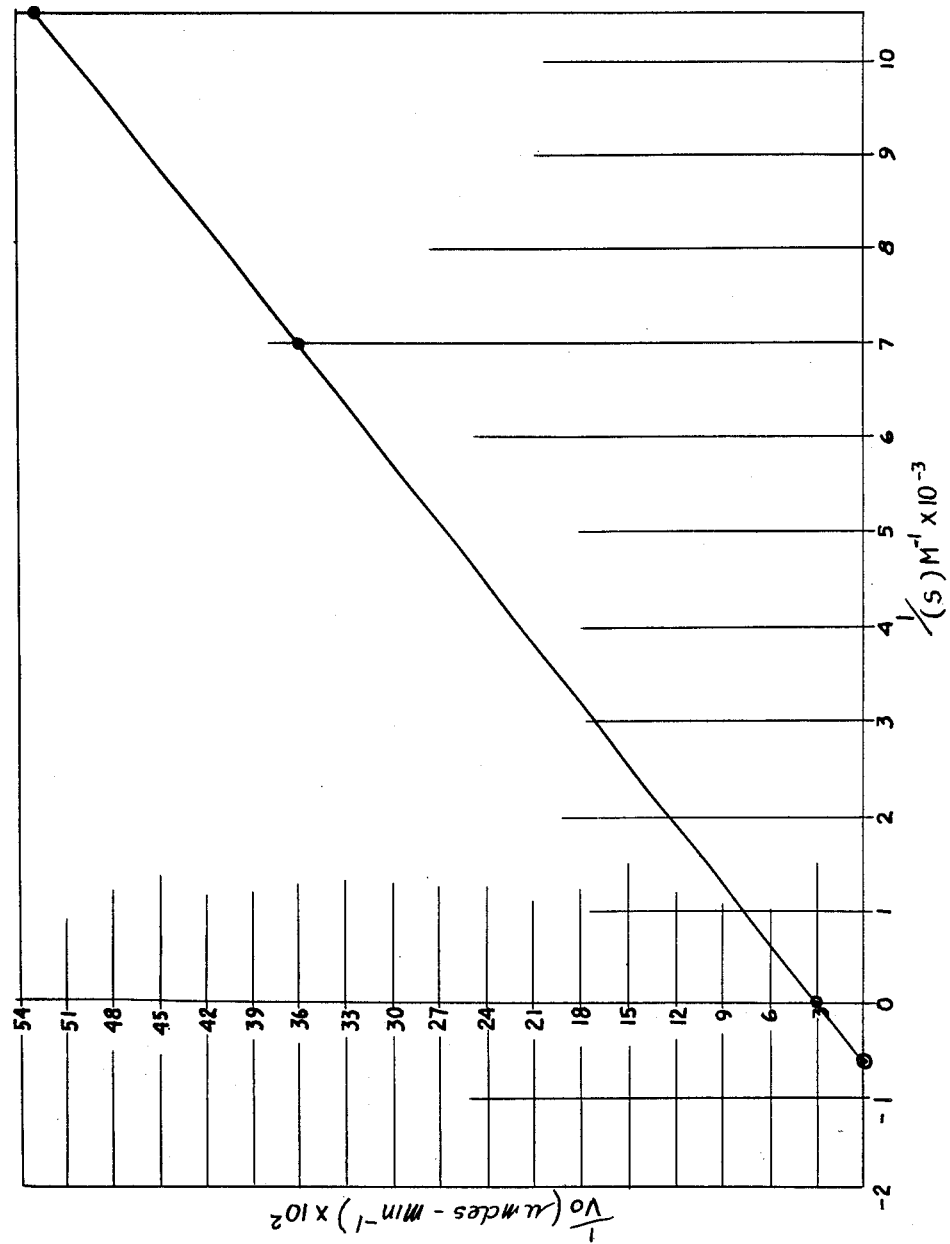
FIG. 6 is a graphic representation of inverse mitochondrial reaction velocity $V_o$ versus inverse substrate concentration, in the determination of $K_m$ and $V_{max}$ for mitochondrial ascorbate production from L-galactono-1,4-lactone.

A typical assay is shown in FIG. 2. The specific activity of this sample was calculated to be $2.5 \times 10^{-3}$ micromoles/min/mg protein. The temperature optimum was determined to be 37° C. as shown in FIG. 3. The pH optimum was determined to be 6.8 as shown in FIG. 4. The kinetic parameters $K_M$ and $V_{max}$ for the mitochondrial system were determined using substrate concentrations ranging from 0.1 mM to 50 mM L-galactono-1,4-lactone. The kinetic parameter $K_M$ was determined to be $1.6 \times 10^{-3}$ M and the kinetic parameter $V_{max}$ was determined to be 0.34 micromoles/min (FIGS. 4, 5 and 6).

After establishing these kinetic parameters for the intact mitochondrial system, the enzyme was further purified by releasing the enzyme activity from the mitochondria. Sonication and various detergents were tested in attempts to solubilize the enzyme.

A series of 5 detergents: (1) nonylphenol POE-9 (NP-9), (2) polydet (P-40), (3) octylglucoside, (4) (3-[3-cholamindopropyl)-dimethylammonio]1-propane sulfonate (CHAPS), and (5) (3-[3-cholamindopropyl)-dimethyl ammonio]-2-hydroxy-1-propane sulfonate).2-H₂O (CHAPSO) were tested. CHAPSO was found to be particularly effective. The results are summarized in Table VII. In addition, CHAPSO released the enzyme selectively from the mitochondria yielding a preparation that had a specific activity 16 times greater than that in Nishikimi, et al. at this stage [Arch. Biochem. & Biophys., 191, 47a (1978)]. A comparison of the oxidase properties of a variety of yeast strains is presented in Table VII.

TABLE VII

| Comparison of L-Galactono-1,4-Lactone Oxidase Activities from Various Yeast Strains | | | |
|---|---|---|---|
| Strain | Km(mM) | Specific Activity (Units/mg Prot.)* × 1000 | Units/gm Cells (Wet) |
| S. cerevisiae (Red Star) | 1.6 | 1.5–4.9 | 0.023 |
| Literature (Nishikimi, et al.) | — | 2.3 | 0.01 |
| C. utilis (NRRL Y-900) | — | 2.6–3.9 | 0.020 |
| C. norvegensis (CBS 1911) | 1.3 | 2.1–5.3 | 0.021 |
| C. norvegensis (MF-42) | — | 6.6 | 0.020 |
| C. norvegensis | — | 7.3–8.3 | 0.021 |

TABLE VII-continued
Comparison of L-Galactono-1,4-Lactone Oxidase Activities from Various Yeast Strains

| Strain | Km(mM) | Specific Activity (Units/mg Prot.)* × 1000 | Units/gm Cells (Wet) |
|---|---|---|---|
| (MF-64) | | | |

*1 unit = 1 micromole/min
The temperature optimum and the pH optimum for the enzymes of each of the strains of Table VII were found to be 37° C. and pH 6.8, respectively.

Yeast mitochondria or more purified enzymes may be used in preparation of an immobilized L-galactono-1,4-lactone oxidase column for the continuous production of L-ascorbic acid, as illustrated by the following example.

EXAMPLE IX

A 10 ml mitochondrial suspension as prepared in the previous Example VIII, containing 1.1 gm of protein, was mixed with 50 ml of a 5% solution of Na-Alginate. This mix was extruded through an 18 gauge needle into 1 liter of 0.25 M sucrose, 0.1 M $CaCl_2$ and 10 mM PIPES pH 6.8 and stirred for 24 hours at 4° C. This produced uniform beads with a diameter of 3 mm.

To demonstrate a "batch" bioconversion utilizing the immobilized mitochondrial enzyme, two grams of beads, containing 0.11 gm of protein, were shaken in 3 ml of the standard reaction mixture for 20 minutes at 37° C. Assays indicated that there was 77 ug/ml of L-Ascorbate in the supernatant.

To demonstrate a continuous bioconversion process using immobilized mitochondrial enzyme, a 0.9 × 30 cm column was packed with the beads and maintained at 37° C. A feed stream containing 2 mM L-galactono-1,4,-lactone and 10 mM piperazine-$N_3N'$-bis[2-ethanesulfonic acid](PIPES) pH 6.8 was pumped through the column. At a flow rate of 3.2 ml/min., L-ascorbate in the effluent increased to 53 ug/ml after 5 minutes.

EXAMPLE X

Two yeast strains, Candida norvegensis CBS 1911 and Candida utilus NRRL Y-900 are utilized with an ethanol carbon source in separate bioconversion runs with each of two different substrates, L-galactono-1,4-lactone or D-galacturonic acid-methyl ester. The bioconversion runs are carried out under aerobic conditions in a 500 milliliter low actinic flask containing 50 ml of the bioconversion medium. The bioconversions were carried out at a temperature of 30° C. for 48 hours with agitation provided by a skaker operating at 200 rpm. The medium for the C. norvegensis runs was the SM1 medium previously described plus 1.5% ethanol plus 0.5% substrate. The medium for the C. utilus runs were SM1 plus 1.5% ethanol plus 0.2% substrate. The results are as follows:

| | CBS 1911 | CBS 1911 | NRRL Y-900 | NRRL Y-900 |
|---|---|---|---|---|
| Substrate | 1* | 2** | 1* | 2** |
| Optical Density | 2.05 | 2.60 | 8.50 | 8.50 |
| L-Ascorbate ug/ml*** | 92.8 | 3.5 | 50.0 | 12.0 |
| Other redox Compounds ug/ml | 10.1 | 17.5 | 1.8 | 1.3 |
| Total Ascorbate ug/100 ml | 10,625 | 473 | 15,905 | 4,383 |

*L-galactono-1,4-lactone
**D-galacturonic acid-methyl ester
***Ascorbate was determined by HPLC analysis with electrochemical detection It will be appreciated from the previous description that in accordance with the present invention, useful new methods, organisms and culture media have been provided for the manufacture of ascorbic acid. While various aspects of the invention have been specifically described with respect to certain specific embodiments, it will be appreciated that various modifications and adaptations will become apparent from the present disclosure, which are within the spirit and scope of the present invention and are intended to be within the scope of the following claims.

What is claimed is:

1. A bioconversion method for producing L-Ascorbic acid, comprising the steps of providing a L-galactono-1,4-oxidase enzyme from a yeast of the strain Candida norvegensis MF-56 ATCC 20686, MF-78 ATCC 20732 or an L-ascorbic acid overproductive mutant strain related thereto having an activity of at least about $6.6 \times 10^3$ micromoles/min/mg protein, immobilizing said enzyme to form an immobilized enzyme, contacting said immobilized enzyme with said aqueous bioconversion medium containing at least about 2.0 millimolar L-galactono-1,4-lactone, maintaining an oxygen level of at least about 3.0 ppm in said bioconversion medium in contact with said immobilized enzyme to convert said L-galactono1,4-lactone to L-Ascorbic acid under oxygenated conditions, and recovering said L-Ascorbic acid.

2. A method in accordance with claim 1 wherein said bioconversion medium has a pH in the range of from about 6.0 to about 7.5.

3. A method in accordance with claim 2 wherein said immobilized enzyme is in the form of beads positioned in a treatment column, and wherein said medium is conducted through said column.

4. A method in accordance with claim 1 wherein said oxygen level is maintained by oxygen-enriched gas.

5. A bioconversion method for producing L-Ascorbic acid, comprising the steps of providing a L-galactono-1,4-oxidase enzyme from a yeast of the strain Candida norvegensis MF-56 ATCC 20686, MF-78 ATCC 20732 or an L-ascorbic acid overproductive mutant strain related thereto having an activity of at least about $6.6 \times 10^3$ micromoles/min/mg protein, immobilizing said enzyme to form an immobilized enzyme, contacting said immobilized enzyme with said aqueous bioconversion medium containing at least about 2.0 millimolar L-galactono-1,4-lactone, maintaining an oxygen level of at least about 20 percent oxygen saturation in said bioconversion medium in contact with said immobilized enzyme to convert said L-galactono-1,4-lactone to L-Ascorbic acid under oxygenated conditions, and recovering said L-Ascorbic acid.

6. A method in accordance with claim 5 wherein said oxygen level is maintained at from about 20 to about 30 percent of oxygen saturation.

7. A method in accordance with claim 6 wherein said bioconversion medium has a pH in the range of from about 6.0 to about 7.5.

8. A method in accordance with claim 6 wherein said immobilized enzyme is in the form of beads positioned in a treatment column, and wherein said medium is conducted through said column.

9. A method in accordance with claim 6 wherein said oxygen level is maintained by oxygen-enriched gas.

* * * * *

UNITED STATES PATENT AND TRADEMARK OFFICE
CERTIFICATE OF CORRECTION

PATENT NO. : 4,916,068
DATED : April 10, 1990
INVENTOR(S) : John F. Roland et al.

It is certified that error appears in the above-identified patent and that said Letters Patent is hereby corrected as shown below:

IN THE SPECIFICATION:

Column 1, line 48, change "BiPhys.," to --Biophys.,--.
Column 2, line 5, change "2,681,058" to --2,681,858--.
Column 2, line 25, change "Of" to --of--.
Column 4, line 51, change "Candida norvegensis" to --Candida norvegensis--.
Column 4, line 63, change "Geneaology" to --Genealogy--.
Column 5, line 25, change "over producing" to --over-producing--.
Column 5, line 31, change "mutagenicly" to --mutagenically--.
Column 5, line 41, change "geneology" to --genealogy--.
Column 6, line 23, change "Geneaology" to --Genealogy--.
Column 6, line 28, change "MF-57$_{(UV/Vn+2\ Res)}$" to --MF-57$_{(UV/VN^{+2}\ Res)}$--.
Column 6, line 36, change "preceeding" to --preceding--.
Column 6, line 40, change "Ni+2" to NI$^{+2}$--.
Column 6, line 41, change "Ce-137" to --Ce137--.
Column 6, line 42, change "Vn+2" to --Vn$^{+2}$--.
Column 6, line 52, change "taxononomic" to --taxonomic--.

UNITED STATES PATENT AND TRADEMARK OFFICE
CERTIFICATE OF CORRECTION

PATENT NO. : 4,916,068

DATED : April 10, 1990

INVENTOR(S) : John F. Roland et al.

It is certified that error appears in the above-identified patent and that said Letters Patent is hereby corrected as shown below:

Column 6, line 55, change "(Ed)" to --(Ed.)--.

Column 7, line 9, after "Melibiose", insert in second column -- - --.

Column 7, line 9, delete "-" in front of "Methyl" in third column.

Column 8, line 21, change "Co." to --Co--.

Column 8, line 32, change "G.L.$^{-1}$" to --gL$^{-1}$--.

Column 8, line 42, change "ZuSo$_4$.5H$_2$O" to --ZuSO$_4$.5H$_2$O--.

Column 8, line 43, change "CUSO$_4$.5H$_2$O" to --CuSO$_4$.5H$_2$O--.

Column 8, line 45, change "(NH$_4$)$_6$MO$_7$O$_{24}$.4H$_2$O" to (NH)$_6$Mo$_7$O$_{24}$.4H$_2$O--.

Column 10, line 7, change

"oxidation $\frac{+O}{-tH}$"

to

-- oxidation $\frac{+O}{-2H}$ --

Column 11, line 60, change "by product" to --byproduct--.

Column 12, line 29, change "ethanl" to --ethanol--.

Column 13, line 52, change "30-Liter" to --30-liter--.

Column 14, line 19, delete space between "g" and "L$^{-1}$".

UNITED STATES PATENT AND TRADEMARK OFFICE
CERTIFICATE OF CORRECTION

PATENT NO. : 4,916,068      Page 3 of 4
DATED : April 10, 1990
INVENTOR(S) : John F. Roland et al.

It is certified that error appears in the above-identified patent and that said Letters Patent is hereby corrected as shown below:

Column 14, line 26, delete "L".

Column 15, line 30, change "galactano" to --galactono--.

Column 15, line 55, change "utiliis" to --utilis--.

Column 16, line 29, change "G-Agar" to --G-agar--.

Column 16, line 62, change "G-Agar" to --G-agar--.

Column 16, line 68, change "MgSO4.7H$_2$O" to --MgSO$_4$.7H$_2$O--.

Column 17, line 22, change "L-Ascorbic" to --L-ascorbic--.

Column 17, line 29, after "sterilized", insert --1.5% ethanol w/v and 1.5% L-galactono-1,4-lactone were--.

Column 17, line 46, change "dichloro-indophenol" to --cichloroindophenol--.

Column 18, line 4, change "Shar-les" to --Sharples--.

Column 18, line 39, change "dimethylammonio" to --dimethyl ammonio--.

Column 18, line 41, delete ")".

Column 19, lines 30, 31, change "L-Ascorbate" to --L-ascorbate--.

Column 19, line 51, change "skaker" to --shaker--.

Column 19, line 52, change "SM1" to --SM-1--.

Column 19, line 54, change "SM1" to --SM-1--.

UNITED STATES PATENT AND TRADEMARK OFFICE
CERTIFICATE OF CORRECTION

PATENT NO. : 4,916,068

DATED : April 10, 1990

INVENTOR(S) : John F. Roland et al.

It is certified that error appears in the above-identified patent and that said Letters Patent is hereby corrected as shown below:

IN THE CLAIMS:

Claim 1, Column 20, lines 19, 20, change "L-Ascorbic" to --L-ascorbic--.

Claim 1, Column 20, lines 31-32, change "L-Ascorbic" to --L-ascorbic--.

Claim 5, Column 20, lines 42, 43, change "L-Ascorbic" to --L-ascorbic--.

Claim 5, Column 20, lines 54, 55, change "L-Ascorbic" to --L-ascorbic--.

Claim 5, line 56, change "L-Ascorbic" to --L-ascorbic--.

Signed and Sealed this

Twelfth Day of November, 1991

Attest:

HARRY F. MANBECK, JR.

*Attesting Officer*   *Commissioner of Patents and Trademarks*